United States Patent
Gumbrecht

(10) Patent No.: US 6,599,746 B1
(45) Date of Patent: Jul. 29, 2003

(54) CALIBRATION FLUID FOR CALIBRATING A SENSOR FOR MEASURING A BLOOD VALUE AND METHODS FOR PRODUCING AND USING THE FLUID

(76) Inventor: Walter Gumbrecht, In der Röte 1, D-91074 Herzogenaurach, Bundesrepublik Deutschland (DE)

(*) Notice: Subject to any disclaimer, the term of this patent is extended or adjusted under 35 U.S.C. 154(b) by 0 days.

(21) Appl. No.: 09/701,882

(22) PCT Filed: Jun. 2, 1999

(86) PCT No.: PCT/DE99/01635

§ 371 (c)(1),
(2), (4) Date: Dec. 4, 2000

(87) PCT Pub. No.: WO99/62398

PCT Pub. Date: Dec. 9, 1999

(30) Foreign Application Priority Data

Jun. 4, 1998 (DE) .......................................... 198 25 014

(51) Int. Cl.⁷ ............................................... G01N 31/00
(52) U.S. Cl. ............................. 436/19; 436/8; 436/149; 436/150; 252/408.1
(58) Field of Search .............................. 436/8, 19, 149, 436/150; 252/408.1; 422/98; 73/1.06, 19.1

(56) References Cited

U.S. PATENT DOCUMENTS

| 4,626,512 A | 12/1986 | Oku et al. |
| 4,871,439 A | 10/1989 | Enzer et al. |
| 5,132,000 A | 7/1992 | Sone et al. |
| 5,212,092 A | 5/1993 | Jackson et al. |
| 5,330,634 A | 7/1994 | Wong et al. |
| 5,385,659 A | 1/1995 | Gumbrecht et al. |
| 5,505,828 A | 4/1996 | Wong et al. |
| 5,658,451 A | 8/1997 | Leiner |
| 5,763,760 A | 6/1998 | Gumbrecht et al. |

FOREIGN PATENT DOCUMENTS

| EP | 0 362 032 | | 4/1990 |
| EP | 0 571 066 | | 11/1993 |
| EP | 0 657 030 | | 1/1997 |
| EP | 0 790 499 | | 8/1997 |
| GB | 2031148 | * | 4/1980 |
| JP | 61034455 | | 2/1986 |

OTHER PUBLICATIONS

Koryta, *Medical and Biological Applications of Electrochemical Devices*, John Wiley & Sons 1980, pp. 13; 21; 82.

Müller–Plathe, "Säure–Basen–Haushalt und Blutgase", 1982, pp. 25–32.

* cited by examiner

Primary Examiner—Maureen M. Wallenhorst
(74) Attorney, Agent, or Firm—Baker Botts LLP

(57) ABSTRACT

The calibration fluid is composed of a biocompatible electrolyte that, at 37° C., exhibits a concentration of bicarbonate ions that lies in the normal physiological range of the concentration of the bicarbonate ions of the blood, exhibits a pH value that lies within a pH value range within 2 through 13 containing the value 7.41 and has a specific ionic strength. In order to enable a calibration of the sensor with a higher precision compared to a known calibration fluid of this type both in vivo as well as in vitro, the ionic strength of the fluid at 37° C. is selected such that it lies in the normal physiological range of the ionic strength of the blood.

10 Claims, 2 Drawing Sheets

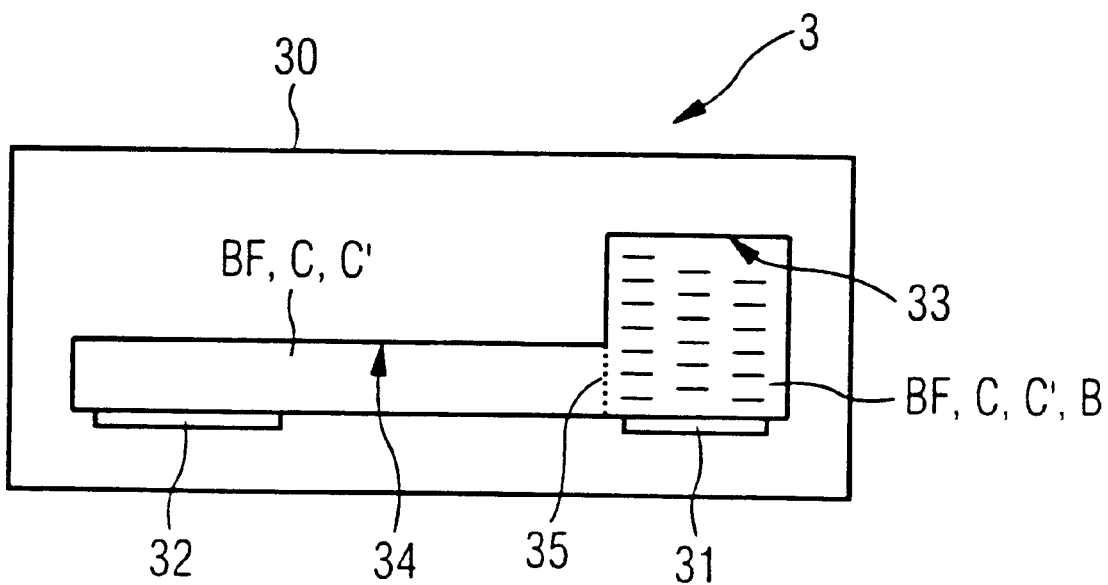

CALIBRATION FLUID FOR CALIBRATING A SENSOR FOR MEASURING A BLOOD VALUE AND METHODS FOR PRODUCING AND USING THE FLUID

BACKGROUND OF THE INVENTION

The invention is directed to a calibration fluid for a calibration of a sensor for measuring a blood value, an application of the fluid and a method for the production of the fluid.

EP 0 657 030 B1 discloses a calibration fluid for a calibration of a sensor for measuring a blood value that comprises a biocompatible electrolyte that, for example, is composed of a Ringer, Ringer Lactate or Ringer Acetate infusion solution and a biocompatible carbon dioxide source that is added to this solution, this generating bicarbonate ions ($HCO_3^{-ions}$) in a specific concentration and carbon dioxide ($CO^2$) with a specific partial pressure $pCO_2$ in the solution.

The compositions of biocompatible electrolytes employed as infusion solutions can be derived from the product descriptions of the various pharmaceutical companies such as, for example, Pharmacia, Braun, Fresenius, Baxter, etc. The composition of blood or blood plasma in view of the pH value, carbon dioxide partial pressure $pCO_2$ and concentrations of the ions contained in the blood is described, for example, in Koryta, "Medical and Biological Applications of Electrochemical Devices", John Wiley & Sons, 1980, page 82.

Given a specific example of the calibration fluid according to EP 0 657 030 B1 (see page 4, lines 2–7 therein), the fluid is composed of 500 ml Ringer Lactate solution to which 10 ml of 8.4% $NaHCO_3$ are added as carbon dioxide source. The added quantity of $NaHCO_3$ corresponds to approximately 20 mmol/l that is contained in the Ringer lactate solution and temporarily stabilizes the unstable pH value of such a solution.

$HCO_3^-$ ions are not contained in traditional physiological electrolytes such as Ringer solutions but are contained in blood plasma. The normal physiological concentration of the $HCO_3^-$ ions in blood plasma lies at 24 mmol/l and can fluctuate within a concentration range containing this concentration value that is still viewed as being physiologically normal.

Given the specific example of the calibration fluid according to EP 0 657 030 B1, the 20 mmol/l $NaHCO_3$ added to the original electrolyte free of $HCO_3^-$ ions generate $HCO_3^-$ ions in the electrolyte in a concentration that still lies in the normal physiological range of the concentration of the $HCO_3^-$ ions in blood plasma at 37° C.

In the specific example of the calibration fluid according to EP 0 657 030 B1, the concentration of the $HCO_3^-$ ions at 37° C. is so high that this fluid—according to the known Henderson-Hasselbalch equation (see, for example, Muller-Plathe, "Säure-Basen-Haushalt und Blutgase", Thieme Verlag, 1982, for example page 32)—has a pH value of 7.95 at this temperature and a value of the $pCO_2$ of $1.2 \cdot 10^3$ Pa (=9 mmHg), these values remaining stable, for example, over a time span of 18 hours.

The pH value of the fluid can be lowered to approximately 7.1 by adding another agent for regulating the pH value, for example sodium or potassium phosphate, so that it is possible to hold the $pCO_2$ to more than $7.33 \cdot 10^3$ Pa (=55 mmHg). In this case, however, there is no longer a fluid according to the preamble of claim 1, since the concentration of the $HCO_3^-$ ions does not lie in the normal physiological range of this concentration, for example in the range 24 mmol/l±5 mmol/l.

The normal physiological pH value of blood, which is recited as 7.41 at 37° C. in many medical textbooks, falls into the pH range between 7.1 and 7.95.

Biocompatible or, respectively, physiological electrolytes such as Ringer solutions are often stored in plastic bags and are air-saturated. At 22° C. and $760 \cdot (4/3) \cdot 10^2$ Pa (760 mmHg) air pressure, a partial pressure composition for this electrolyte derives as $155 \cdot (4/3) \cdot 10^2$ Pa (155 mmHg) $pO_2$ $585 \cdot (4/3) \cdot 10^2$ Pa (585 mmHg) $pN_2$ $20 \cdot (4/3) \cdot 10^2$ Pa (20 mmHg) $pH_2O$, i.e.

$760 \cdot (4/3) \cdot 10^2$ Pa (760 mmHg).

overall $pO_2$ is thereby the partial pressure of the oxygen, $pN_2$ is the partial pressure of the nitrogen and $pH_2O$ is the partial pressure of water.

By adding the 20 mmol/l $NaHCO_3$ to such an electrolyte, $9 \cdot (4/3) \cdot 10^2$ Pa (9 mmHg) $pCO_2$ is added to the sum of these partial pressures or—given the presence of the inorganic phosphate buffer—$55 \cdot (4/3) \cdot 10^2$ Pa (55 mmHg) $pCO_2$ is added thereto. The atmospheric pressure that is respectively present and bears on the fluid is thereby exceeded, and an exhalation of gases of the fluid, i.e. a bubble formation in the fluid, can occur.

Physiological electrolytes such as Ringer solutions exhibit an ion intensity that is usually equal to the normal physiological ion intensity of blood, this lying at 155 mmol/l and potentially fluctuating within an ion intensity range containing this ion intensity value that is still considered physiologically normal.

The addition of the 20 mmol/l $NaHCO_3$ to such an electrolyte raises the ion intensity of the calibration fluid resulting therefrom by 20 mmol/l to non-physiological values that, for example, lie between 165 mmol/l and 185 mmol/l.

In physiological electrolytes such as Ringer solutions, moreover, the concentration of $Na^+$ ions is usually selected equal to the normal physiological concentration of the blood, this lying at 140 mmol/l. The addition of the 20 mmol/l $NaHCO_3$ to the electrolyte increases the concentration of the $Na^+$ ions in the calibration fluid resulting therefrom from the normal 140 mmol/l to non-physiological 160 mmol/l.

Moreover, physiological electrolytes such as Ringer solutions comprise an osmolarity that is selected equal to the normal physiological osmolarity of blood plasma, this lying at 295 mosmol/l and potentially fluctuating within an osmolarity range containing this osmolarity value that is still considered physiologically normal.

The addition of the 20 mmol/l $NaHCO_3$ to such an electrolyte raises the osmolarity of the calibration fluid resulting therefrom by $2 \cdot 20$ mosmol/l=40 mosmol/l to non-physiological values that, for example, lie between 315 mosmol/l and 355 mosmol/l.

The known calibration fluid can be infused, and sensors for measuring the $pCO_2$ of blood can be calibrated with this fluid not only in vitro but also in vivo.

SUMMARY OF THE INVENTION

An object of the invention is to offer calibration fluid that enables a calibration of the sensor with a precision that is higher compared to the known calibration fluid.

This object is achieved by the calibration fluid compose of a bio-compatible electrolyte that at 37° C. has a concentration of bicarbonate ions that lies in a range of 24 mmol/l±5 mmol/l, a pH value that lies in a pH range within 5 through 9 and contains a value of 7.41; and an ion intensity that lies in a range of 155 mmol/l±10 mmol/l.

The normal physiological range of the concentration of bicarbonate ions blood plasma falls in the range of 25 mmol/l±5 mmol/l of the concentration of the bicarbonate ions indicated in claim 1, and the normal physiological range of the ion intensity (ionic strength) of the blood falls in the recited range of 155 mmol/l±10 mmol/l, and it can be expedient to select a value lying optimally close to 155 mmol/l for the concentration of the bicarbonate ions and to select a value lying optimally close to 155 mmol/l for the ion intensity.

The specific example of a calibration fluid known from EP 0 657 030 B1 and the inventive calibration fluid differ essentially in that the ion intensity in the known calibration fluid—differing from the inventive calibration fluid—does not lie in the range of 155 mmol/l±10 mmol/l but outside this range.

The inventive calibration fluid is based on the perception resulting from Nernst's equation (see Koryta, pages 13 ff) that, given potentiometric determination of the unknown pH value and/or of an unknown concentration of an ion type of a fluid such as, for example, blood with the assistance of a fluid having a known pH value and/or of a known concentration of this ion type—the concentrations of the two fluids can only be directly compared to one another and a correct concentration result with respect to the unknown fluid can only be obtained with the ion intensities of the two fluids are at least approximately equal to one another from the very outset.

Since the ion intensity given the inventive calibration fluid lies in the range 155 mmol/±10 mmol/l, this fluid exhibits essentially the same ion intensity as the blood. A deviation of the ion intensity of the inventive calibration fluid from the value of the normal physiological ion intensity of the blood that is actually present is permissible with reference to an adequate potentiometric measuring precision as long as the ion intensity of the fluid remains in the range 155 mmol/l±10 mmol/l.

When, in contrast, the ion intensity of the calibration fluid lies outside the range 155 mmol/l±10 mmol/l, measuring errors can occur that falsify the potentiometric measured result.

Preferably and advantageously, the inventive calibration fluid is fashioned such that the ion types contained in the blood are present in concentrations in the fluid that deviate so little from the normal physiological concentrations of these ion types in the blood that, given a contact between the fluid and the blood, a diffusion voltage of less than 1 mV occurs at the boundary surface between the fluid and the blood.

This measure is based on the perception resulting from the Henderson equation (see Koryta, pages 21 f) that, given what is not a negligibly diffusion voltage between fluid and blood, this voltage acts as a measuring error at least where the calibration fluid is employed as a bridge electrolyte between a reference electrode and the blood and that this measuring error is negligible when the diffusion voltage is lower than 1 mV.

A diffusion voltage that is not negligibly high occurs at the boundary between fluid and blood when, for example, the ion composition of the fluid does not fall within the range of the normal physiological ion composition of the blood, whereby it already suffices when the concentration of only a single ion type of the fluid, for example, the $Na^+$ ions—lies adequately far outside the range of the normal physiological concentration of this ion type in the blood.

Preferably and advantageously, the inventive calibration fluid exhibits an osmolarity that lies in the range 295 mosmol/l±20 mosmol/l into which the normal physiological range of the osmolarity of blood plasma falls. This has the advantage that the osmolarity of the fluid lies in the range of an osmolarity of a sensor for measuring a blood value and, consequently, no disturbing effects due to osmotic pressure differences occur given contact of the fluid with this sensor. It can be expedient to select a value for the osmolarity that lies optimally close to 295 mosmol/l.

The inventive fluid can advantageously comprise a pH value in the range between 6.6 and 8.0 which is advantageously greater than the range between 7.1 and 7.95 disclosed by EP 0 657 030 B1.

An especially advantageous and preferred embodiment of an inventive calibration fluid comprises a physiological organic buffer that is preferably defined by a specific Tris/TrisH$^+$ ratio or by a specific R-PO$_4^{2-}$/R-HPO$_4^-$ ratio. R stands for a selectable organic radical.

Like calibration fluids that are usually employed, the inventive calibration fluid is usually produced at room temperature (standard value 22° C.) and stored thereat such that, at this temperature, it comprises a sum of all partial pressures that is equal to the pressure bearing on the fluid while being stored, this usually being the local atmospheric pressure (standard value 760·(4/3)·10$^2$ Pa=760 mmHg).

The calibration fluid is expediently heated to 37° C. in the sensor means, for example in a full-through channel of this means, in order to assure a calibration of a sensor at the standard body temperature at which the blood values are also measured.

The heating of the calibration fluid from 22° C. to 37° C. in the sensor means ensues suddenly and without the possibility of a gas exchange with the ambient air. This results in a sudden increase in the sum of all partial pressures of the fluid.

When the elevated sum of all partial pressures of the fluid is higher than the pressure bearing on the fluid, this can lead to exhalation of gas from the fluid and to a formation of bubbles in the fluid. This is one possibility for the creation of gas bubbles that arise at the sensor itself and/or can be transported to the sensor with the fluid.

Another possibility for the creation of gas bubbles at the sensor is, for example, an inclusion of air or of some other gas in the calibration fluid and transport of this enclosed gas together with the fluid to the sensor.

A bubble pressure that is equal to the pressure bearing on the fluid at the sensor prevails in a gas bubble stuck to the sensor. Given sensor devices wherein the blood values are measured in vitro, this is usually equal to the pressure bearing on the fluid while being stored, usually the local atmospheric pressure; given sensor devices wherein the blood values are measured in vivo, this is usually equal to the pressure bearing on the fluid during storage plus the average blood pressure (approximately 100·(4/3)·10$^2$ Pa=100 mmHg) in the blood vessel that is in communication with the sensor.

Gas bubbles at the sensor during the calibration can lead to considerable calibration errors that produce uncontrollable measuring errors in a subsequent blood value measurement.

Given an inventive calibration fluid, the risk of a creation of calibration errors due to gas bubbles can be advantageously reduced in that the sum of all partial pressures of the fluid is lower than a pressure that bears on the fluid.

This measure advantageously assures that no gas bubbles arise in the fluid due to exhalation of gas of the fluid or assures that gas bubbles already present, for example enclosed air, disappear due to absorption in the fluid. This is also particularly true when the fluid for calibration of the sensor is preferably heated to 37° C. at the sensor in order to assure a calibration at the standard body temperature.

The sum of all partial pressures of the fluid should at least be lower than the pressure that bears on the fluid at the sensor. This assures that gas bubbles cannot arise, at least at the sensor.

When, in this case, gas bubbles have arisen in the fluid at a location other than at the sensor and when these proceed to the sensor, on the other hand, they are absorbed by the fluid at the sensor and advantageously disappear by themselves, since, of course, the pressure bearing on the fluid at the sensor is higher than the sum of all partial pressures of the fluid.

Gas bubbles can arise in the fluid due to gas inclusion at the other location or—since the sum of all partial pressures of the fluid is higher than the pressure bearing on the fluid at this location, can arise due to exhalation of gases from the fluid.

An exhalation of gases from the fluid can be absolutely prevented when the sum of all partial pressures of the fluid is selected lower than the lowest pressure bearing on the fluid. In this case, gas bubbles due to exhalation of the fluid cannot arise anywhere in the fluid and gas bubbles that have arisen due to gas inclusion are immediately absorbed in the fluid and disappear not only at the sensor but everywhere, since the sum of all partial pressures of the fluid is lower everywhere than the pressure bearing on the fluid.

The sum of all partial pressures of the fluid is temperature-dependent and increases with increasing temperature. This temperature dependency must be taken in to consideration. The determining factor is the temperature prevailing at the sensor. It must be assured that the sum of all partial pressures of the fluid at the sensor at this temperature is lower than the pressure that bears on the fluid at the sensor.

The temperature prevailing at the sensor is the determining factor. It must be assured that the sum of all partial pressures of the fluid at this temperature at the sensor is lower than the pressure that bears on the fluid at the sensor.

The sum of all partial pressures of the inventive calibration fluid is composed at least of the partial pressure of a solvent, for example water, and a non-disappearing partial pressure $pCO_2$ of the carbon dioxide.

It is advantageous when the partial pressure of the $N_2$ at 37° C. in the inventive calibration fluid is lower than the normal physiological value of this pressure in the blood at this temperature. The normal physiological value of the partial pressure of $N_2$ in blood at 37° C. amounts to about $573 \cdot (4/3) \cdot 10^2$ Pa (537 mmHg).

This measure offers the following advantages: it is beneficial to select the sum of all partial pressures of the fluid optimally low compared to the pressure bearing on the fluid since an exhalation of gases of the fluid is all the more dependably prevented and an absorption of gas bubbles in the fluid is more assured the higher the difference between the higher, bearing pressure and the smaller sum of all partial pressures of the fluid is.

The partial pressure of the neutral blood gas $N_2$ is, on the one hand, of no significance in the measurement of the blood values; on the other hand, its normal physiological value in the blood is higher than the sum of all other normal physiological partial pressures of the blood that are of significance for measuring the blood values and, for this reason, should also be present in the fluid for a calibration with a partial pressure value that differs from zero.

For this reason, it is expedient to effect the reduction of the sum of all partial pressures of the fluid mainly on the basis of a lowering of the partial pressure of $N_2$.

It is especially advantageous to essentially entirely forego $N_2$ in the fluid, so that the $N_2$ partial pressure of the fluid is essentially equal to zero. In this case, the greatest possible difference between the pressure bearing at the sensor and the sum of all partial pressure of the fluid is advantageously achieved.

An inventive calibration fluid is preferably and advantageously employed as bridge electrode between a reference electrode and a measuring electrode in a potentiometric measuring instrument comprising a reference electrode and a measuring electrode for measuring a blood value.

The inventive calibration fluid, which differs from the traditional calibration fluid, cannot be produced from a traditional physiological electrolyte by simply adding the carbon dioxide source to this electrolyte. A preferred and advantageous method for simple production of the inventive calibration fluid is by dissolving a specific quantity of an essentially salt-free, aqueous solvent $NaHCO_3$ together with at least one other biocompatible salt are of such a weight ratio relative to one another that the solution subsequently exhibits a bicarbonate ion concentration at 37° C. in the normal physiological range of the blood, a pH value in a pH value range within 2 through 13 containing the value 7.41 and an ion intensity in the normal physiological range of the blood.

The inventive calibration fluid generally exhibits the following advantages:

The fluid enables a calibration of a sensor with a higher precision compared to the known calibration fluid, both in vivo as well as in vitro.

Since the ion intensity of the fluid is selected in the range 155 mmol/l±10 mmol/l, a correct concentration result with respect to the blood can always be obtained.

Since the ion types contained in the blood are contained in the fluid in concentrations deviating so little from the normal physiological concentrations of these ion types in the blood that a diffusion voltage of less than 1 mV occurs at the boundary surface between the fluid and the blood given a contact between the fluid and the blood, this diffusion voltage is negligible and no measuring errors caused by diffusion voltage occur when the calibration fluid is employed as a bridge electrolyte between a reference electrode and the blood.

Since the concentration of the bicarbonate ions in the fluid lies in the range 24 mmol/l±5 mmol/l, the effect is that the base excess of the blood is not negatively influenced by the fluid infused into the blood and, consequently, the base excess actually present in the blood can be measured unfalsified, regardless of whether it exhibits the normal physiological value lying at 0 mmol/l or an abnormal, positive or negative value.

The base excess is a metabolic characteristic of blood whose normal physiological value is equal to 0 mmol/l and that can deviate more or less greatly from 0 mmol/l given a metabolic disturbance. A base excess of the blood differing from 0 mmol/l is normalized very slowly via the kidneys, over a course of hours.

Due to the concentration of $HCO3^-$ ions in the fluid being in the range 24 mmol/l±5 mmol/l, no disturbance of the metabolic acid-base economy of the organism is advantageously produced given an infusion of the fluid, this disturbance being capable of being dismantled only very slowly via the kidneys.

The pH value of the fluid can deviate more greatly then previously from the normal physiological 7.41 of the blood. As a result thereof, the sensitivity of a pH value sensor can be advantageously identified in a greater range of measurement with two different pH values.

In particular, the pH value of the fluid in the entire range between 6.6 and 8.0 can advantageously be highly buffered compared to a bicarbonate buffer, so that it can be set with long-term stability. For example, the buffer effect to 20 mmol/l $NaHCO_3$ is very slight because less than 0.3 mmol/l volatile $CO_2$ are present in the fluid at 37° C. By themselves, the 20 mmol/l $NaHCO_3$ produce only a temporarily stable pH value.

The buffer system employed for intense buffering of the pH value of the fluid is physiologically innocuous when the fluid laced with this buffer system exhibits the concentration of $CHO_3^-$ ions lying in the range 24 mmol/l±5 mmol/l. In this case, the blood with the infused, highly buffered fluid is rapidly brought to the normal physiological pH value of 7.41 and to the normal physiological $pCO_2$ of $40 \cdot (4/3) \cdot 10^2$ Pa (40 mmHg) of the blood by the respiratory system, i.e. after passing the lung once, even given a pronounced deviation of the pH value of the fluid from the normal pH value of 7.41. The normal physiological $pCO_2$ is a respiratory characteristic of the blood.

The physiologic, organic buffers are especially suited for intense buffering of the fluid exhibiting the concentration of $HCO_3^-$ ions lying in the range 24 mmol/l±5 mmol/l since they have the advantages that they can be innocuously infused.

The fluid is advantageously physiologically compatible for all patient groups and enables a high precision in the identification of the blood values.

The sum of all partial pressures of the fluid can be advantageously selected lower than the pressure bearing on the fluid at the sensor, so that no gas bubbles arise in the fluid or gas bubbles already present are absorbed in the fluid, these potentially highly falsifying the calibration of the sensor.

The sensors for measuring the following blood values can be advantageously calibrated with the fluid: $pCO_2$, pH value and concentrations of all ion types contained in the blood or blood plasma such as $HCO_3^-$, $Na^+$, $K^+$, $Ca^{2+}$, $Mg^{2+}$, $Cl^-$, $SO_4^{2-}$, $CO_3^{2-}$, etc.

The invention is explained in greater detail by way of example below in the following description with reference to the Figures.

BRIEF DESCRIPTION OF THE DRAWINGS

FIG. 2 is a schematic illustration of a section through a known potentiometric sensor having a measuring and reference electrode wherein an inventive fluid is employed as bridge electrolyte.

DESCRIPTION OF THE PREFERRED EMBODIMENTS

Figure 1:
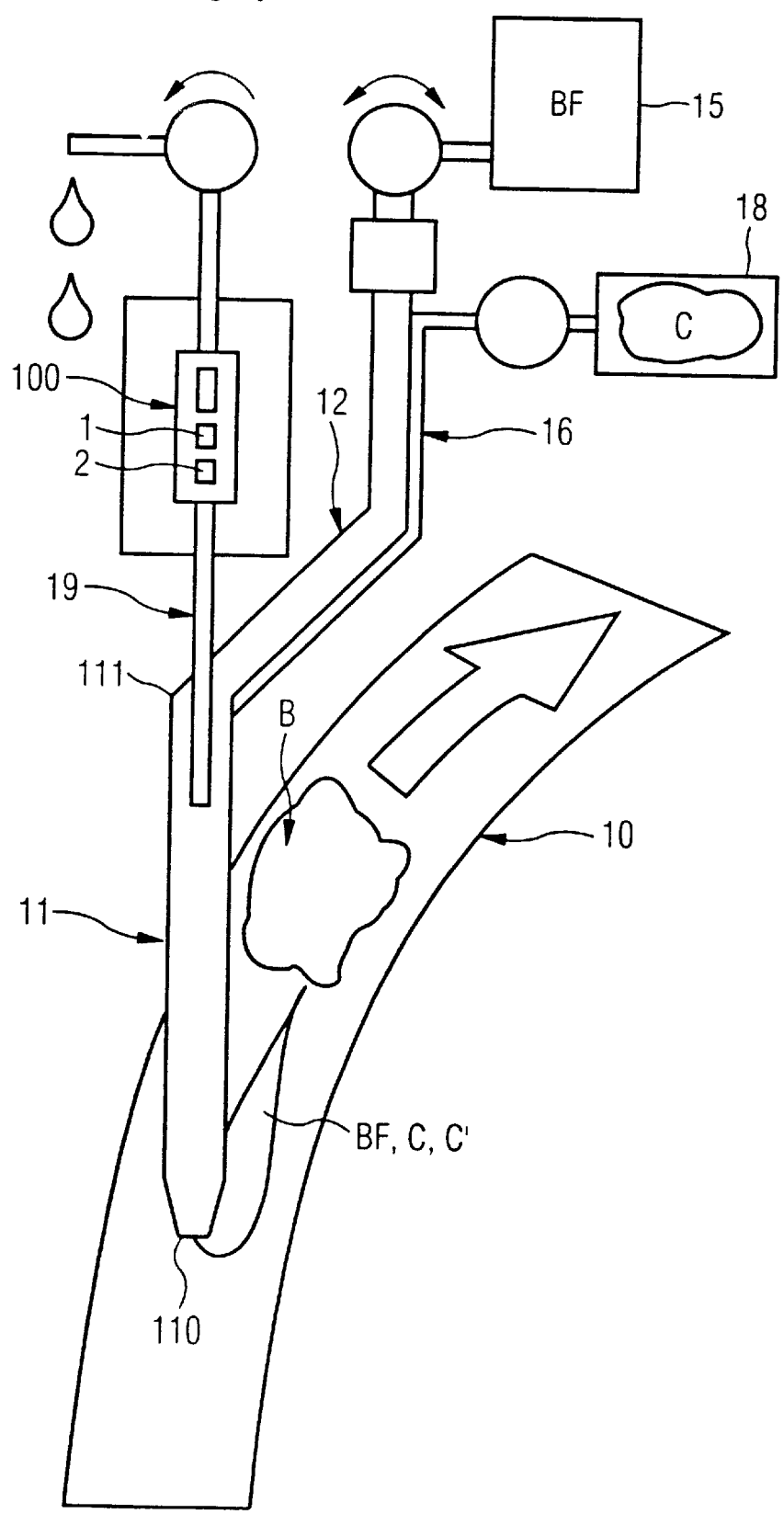
FIG. 1 is a schematic illustration of an apparatus for measuring blood values whose sensors can be calibrated with the assistance of an inventive calibration fluid.

An applied example of the inventive calibration fluid is described below, this referring to EP 0 790 499 A2 whose content is incorporated as part of the specification but only in the relevant parts. The exemplary apparatus shown in the present FIG. 1 is based on FIG. 1 and the appertaining description in EP 0 790 499 A2. The reference characters employed in the present FIG. 1 are identical to the corresponding reference characters of FIG. 1 of EP 0 790 499 A2 and reference the same parts as in EP 0 790 499 A2.

As in EP 0 790 499 A2, a base line fluid and at least one calibration fluid are employed in the present invention for calibrating. According to the present FIG. 1, the base line fluid BF is situated in a gas-tight vessel 15 in the form of a plastic bag; the calibration fluid C is in another gas-tight vessel 18 in the form of a plastic bag. Both fluids BF and C are protected against gas loss in the vessels 15 and 18 during transport, storing and employment.

On the way from the respective vessel 15 or, respectively, 18 to a sensor means 100, each fluid must flow through a respective, gas-permeable hose 12 or, respectively, 16 having the length of 1.5 through 2 m and is thereby subjected to a gas loss.

Due to further boundary conditions of the system, however, the dwell time of the baseline fluid BF in the hose 12 is longer than that of the calibration fluid C in the hose 16. This results therein that the $pCO_2$ of the baseline fluid BF must have a low value insofar as possible in order to keep the gradient relative to the practically $CO_2$-free air as small as possible.

With respect thereto, EP 0 790 499 A2 mentions an "imprecisely defined $pCO_2$ value of less than 10 mmHg" of the baseline fluid BF.

An optimally precisely defined, low value of the $pCO_2$ of the baseline fluid BF is advantageous compared thereto.

By employing an inventive calibration fluid having an organic buffer with a pK value of 7.8 as baseline fluid BF (see the general Henderson-Hasselbalch equation) defined by a Tris/$TrisH^+$ ratio of 1:1, a stable pH value of 7.8 of the baseline fluid BF can be advantageously set given optimum buffering, and exactly defines $pCO_2$ value of $14.1 \cdot (4/3) \cdot 10^2$ Pa (14.1 mmHg) of the baseline fluid BF to be set advantageously according to the Henderson-Hasselbalch equation therefrom because of the concentration of the $HCO_3^-$ ions in the range 24 mmol/l±5 mmol/l that are established in the fluid, this still being low enough in order to minimize a $CO_2$ loss to the air. Moreover, the stability of the value of $pCO_2$ is also influence by the overall concentration of the buffer. The experiences with a Tris concentration of 25 mmol/l have been good.

Apart from the fact that, given adherence to the concentration of the $HCO_3^-$ ions lying in the range 24 mmol/l±5 mmol/l, the normal pH value 7.41 and normal $pCO_2$ of $40 \cdot (4/3) \cdot 10^2$ Pa (40 mmHg) are immediately achieved given passage through the lung, the dose of approximately 5 ml/h through 3 mmol/day given a Tris concentration of, for example, 25 mmol/l amounts to only about 1% of the dose that is administered in the form of pure alkaline Tris in therapy of a metabolic acidosis and corresponds to a Tris concentration of 0.3 mol/l given a pH value of 10 and a base excess of the blood of approximately 300 mmol/l.

Since the calibration fluid C has a shorter dwell time in the hose 16, it can exhibit a higher value of the $pCO_2$ that, moreover, need not exhibit the stability of the baseline fluid BF. An inventive calibration fluid can be employed as calibration fluid C, this potentially comprising—in the simplest case—the normal pH value of 7.41 and—according to the Henderson-Hasselbalch equation—is $pCO_2$ of $40 \cdot (3/4) \cdot$ $10^2$ Pa (40 mmHg) or, for example, pHPCO$_2$[·(3/4)·10$^2$ PaVmmHg]

| pH | pCO$_2$[· (3/4) · 10$^2$ Pa or mmHg] |
|---|---|
| 7.6 | 24 |
| 7.2 | 62 |
| 7.0 | 100 |

Since the $CO_2$ buffer behavior of the calibration fluid C is less critical than in the baseline fluid BF, a potentially utilized pH buffer need not necessarily be fixed at the pK value of the fluid. Preferably, an organic physiological buffer in the form of, for example, a glycero-phosphate buffer is thus employed here, this in fact comprising a pK value of only 6.2 but allowing calcium ions to be employed without having to fear precipitations as in the case of inorganic physiological phosphate buffers.

Let only three specific examples of an inventive calibration fluid and the inventive manufacture thereof be described:

All substances employed for producing the examples correspond to the pharmaceutical regulations that are valid in the respective country of employment.

For producing the first specific example,

| | | |
|---|---|---|
| 557.99 | g | NaCl |
| 37.28 | g | KCl |
| 22.18 | g | MgSO$_4$ * 7H$_2$O |
| 133.63 | g | Na-Acetate * 3H$_2$O |
| 302.85 | g | Tris |
| 207.50 | g | NaHCO$_3$ |
| 1292.35 | g | HCl (1 mol/l HCl) |
| 97.946 | kg | water | are employed as initial materials for, for example, a batch of 100 liters of fluid.

The salts and HCl solution are dissolved in water and subsequently gasified with $CO_2$, $O_2$ dependent on the temperature and pressure, with a suitable relationship of these gases such that the equilibrated solution exhibits a pCO$_2$ value of 14.1 mmHg as well as a suitable PO$_2$ value at 37° C.

Due to the pK values of 7.8 for Tris/TrisH$^+$, 6.08 for HCO$_3^-$/CO$_2$ and the molar solubility coefficient of $CO_2$ in water of 0.0325, the following composition of the fluid derives:

| | | |
|---|---|---|
| 130.00 | mmol/l | Na$^+$ |
| 5.00 | mmol/l | K$^+$ |
| 0.90 | mmol/l | Mg$^{2+}$ |
| 12.50 | mmol/l | Tris |
| 12.50 | mmol/l | TrisH$^+$ |
| 113.20 | mmol/l | Cl$^-$ |
| 0.90 | mmol/l | SO$_4^{2-}$ |
| 9.82 | mmol/l | Acetate$^-$ |
| 0.24 | mmol/l | CO$_3^{2-}$ |
| 24.00 | mmol/l | HCO$_3^-$ |
| pH value = 7.80 | | |
| pCO$_2$ = 14.1 mmHg = 14.1 · (4/3) · 10$^2$ Pas | | |

This fluid is a Ca-free, Tris-buffered calibration fluid. It contains no $N_2$, advantageously does not degasify the gas bubbles at the pressure normally bearing on the fluid at the sensor and/or allows gas bubbles that have arisen in some other way, for example due to air inclusion, to disappear by absorption in the fluid.

The fluid could also contain $N_2$ that, like $CO_2$ and $O_2$, can be introduced into the solution by gasification. In this case, it is also recommendable to select the sum of all partial pressures of the fluid and, over and above this, the partial pressure pN$_2$ of the nitrogen differing from zero so low in comparison to a pressure bearing on the fluid that no exhalation of gases from the fluid can occur and/or gas bubbles that have arisen in some other way are absorbed in the fluid.

With this fluid, the sensors for pCO$_2$, the pH value and the concentration of the ions HCO$_3^-$, Na$^+$, K$^+$, Mg$^{2+}$, Cl$^-$, SO$_4^{2-}$ and CO$_3^{-2}$ present in the blood can be calibrated. Given the calibration method disclosed by EP 0 790 499 A2 wherein the sensitivity of the sensors, particularly of the $CO_2$ sensor, can also be advantageously calibrated, this exemplary fluid is especially suited as baseline fluid since the pCO$_2$ amounts to only 14.1·(4/3)·10$^2$ Pa (14.1 mmHg) and lies adequately close to the value of the pCO$_2$ of air. A different fluid should be employed as calibration fluid C, this differing—for the $CO_2$ sensor, in the value of the pCO$_2$, in the pH value for the pH sensor and/or in the concentration of the ion type for an ion type sensor, namely differing from the baseline fluid BF, so that the $CO_2$ sensor, pH sensor and/or the ion type sensor can be calibrated with this calibration fluid C relative to the baseline fluid BF.

For producing the second specific example,

| | | |
|---|---|---|
| 556.93 | g | NaCl |
| 37.28 | g | KCl |
| 1.47 | g | CaCl2 * 2H$_2$O |
| 22.18 | g | MgSO$_4$ * 7H$_2$O |
| 133.63 | g | Na-Acetate * 3H$_2$O |
| 302.85 | g | Tris |
| 207.50 | g | NaHCO$_3$ |
| 1292.35 | g | HCl (1 mol/l HCl) |
| 97.946 | kg | water | are employed as initial substances for, for example, a batch of 100 liters of fluid.

The salts and HCl solution are dissolved in water and subsequently gasified with $CO_2$, $O_2$ dependent on the temperature and pressure, with a suitable ratio of these gases, such that the equilibrated solution exhibits a pCO$_2$ value of 14.1 mmHg as well as a suitable pO$_2$ value at 37° C.

Due to the pK values of 7.8 for Tris/TrisH$^+$, 6.08 for HCO$_3^-$/CO$_2$ and the molar solubility coefficient of $CO_2$ in water of 0.0325, the following composition of the fluid derives:

This fluid is a Ca-containing, Tris-buffer calibration fluid. It contains no $N_2$, advantageously does not degasify into gas bubbles at the pressure normally bearing on the fluid at the sensor and/or allows gas bubbles that have arisen in some other way, for example by air inclusion, to disappear by absorption in the fluid.

The fluid could also contain $N_2$ that, like $CO_2$ and $O_2$, can be introduced into the solution by gasification. In this case, it is also recommendable to select the sum of all partial pressures of the fluid and, over and above this, the partial pressure pN$_2$ of the nitrogen differing from zero so low in comparison to a pressure bearing on the fluid that no exhalation of gases from the fluid can occur and/or gas bubbles that have arisen in some other way are absorbed in the fluid.

With this fluid, the sensors for pCO$_2$, the pH value and the concentration of the ions HCO$_3^-$, Na$^+$, K$^+$, Mg$^{2+}$, Cl$^-$, SO$_4^{2-}$ and $CO_3^{2-}$ present in the blood can be calibrated. Given the calibration method disclosed by EP 0 790 499 A2, this exemplary fluid is also especially suited as baseline fluid BF since the $pCO_2$ amounts to only $14.1 \cdot (4/3) \cdot 10^2$ Pa (14.1 mmHg) and lies adequately close to the value of the $pCO_2$ of air. Another fluid should also be employed as calibration fluid C here that—for the $CO_2$ sensor—differs in the value of the $pCO_2$, differs in the pH value for the pH sensor and/or differs in the concentration of the ion type for an ion type sensor, differing, namely, from the baseline fluid BF, so that the $CO_2$ sensor, the pH sensor and/or the ion type sensor can be calibrated with this calibration fluid C relative to the baseline fluid BF.

For producing the third specific example,

| | |
|---|---|
| 533.85 g | NaCl |
| 29.82 g | KCl |
| 17.64 g | $CaCl2 * 2H_2O$ |
| 14.79 g | $MgSO_4 * 7H_2O$ |
| 13.61 g | Na-Acetate $* 3H_2O$ |
| 306.12 g | $Na_2$-Glycero-Phosphate $* 5H_2O$ |
| 232.29 g | $NaHCO_3$ |
| 532.38 g | (1 mol/l HCl) |
| 98.986 kg | water | are employed as initial substance for, for example, a batch of 100 liters of fluid.

The salts and HCl solution are dissolved in water and subsequently gasified with $CO_2$, $O_2$ dependent on the temperature and pressure with a suitable ratio of these gases such that the equilibrated solution exhibits a $pCO_2$ value of 112 mmHg as well as a suitable $PO_2$ value at 37° C.

Due to the pK values of 6.2 for $R$-$PO_4^{2-}$/$R$-$HPO_4^-$, 6.08 for $HCO_3^-$/$CO_2$ and the molar solubility coefficient of $CO_2$ in water of 0.0325, the following composition of the solution derives:

| | |
|---|---|
| 140.00 mmol/l | $Na^+$ |
| 4.00 mmol/l | $K^+$ |
| 1.20 mmol/l | $Ca^{2-}$ |
| 0.60 mmol/l | $Mg^{2+}$ |
| 8.35 mmol/l | $R$-$PO_4^{2-}$ |
| 1.65 mmol/l | $R$-$HPO_4^-$ |
| 102.99 mmol/l | $Cl^-$ |
| 0.60 mmol/l | $SO_4^{2-}$ |
| 1.00 mmol/l | $Acetate^-$ |
| 0.03 mmol/l | $CO_3^{2-}$ |
| 24.00 mmol/l | $HCO_3^-$ |
| pH value = 6.9 | |
| $pCO_2 = 112$ mmHg $= 14.1 \cdot (4/3) \cdot 10^2$ Pa | |

This fluid is a Ca-containing, glycero-phosphate-buffered calibration fluid. It contains no $N_2$, advantageously does not degasify into gas bubbles at the pressure normally bearing on the fluid at the sensor and/or allows gas bubbles that have arisen in some other way, for example, by air inclusion, to disappear in the fluid by absorption.

The fluid could also contain $N_2$ that, like $CO_2$ and $O_2$, can be introduced into the solution by gasification. In this case, it is also recommendable to select the sum of all partial pressures of the fluid and, over and above this, the partial pressure $pN_2$ of the nitrogen differing from zero so low in comparison to a pressure bearing on the fluid that no exhalation of gases from the fluid can occur and/or gas bubbles that have arisen in some other way are absorbed in the fluid.

With this fluid, the sensors for $pCO_2$, the pH value and the concentration of the ions $HCO_3^-$, $Na^+$, $K^+$, $Mg^{2+}$, $Cl^-$, $SO_4^{2-}$ and $CO_3^{2-}$ present in the blood can be calibrated. Given the calibration method disclosed by EP 0 790 499 A2, wherein the sensitivity of the sensors, particularly of the $CO_2$ sensor can also be calibrated, this exemplary fluid is especially suited as calibration fluid C, since the $pCO_2$ at $112 \cdot (4/3) \cdot 10^2$ Pa (112 mmHg) lies at a great distance from the value of the $pCO_2$ of air. In this case, the first or second specific example of the inventive fluid can be employed as baseline fluid BF, this differing in the $pCO_2$ for $CO_2$ sensor, and the pH value for the pH sensor and/or in the concentration of the ion type for an ion-type sensor, namely differing from this calibration fluid C, so that the $CO_2$ sensor, pH sensor and/or the ion-type sensor can be calibrated with this calibration fluid C with respect to this respective baseline fluid BF.

As disclosed by EP 0 790 499 A2, an inventive calibration fluid can be brought to each sensor 1, 2, etc. contained in the sensor means 100 through a cannula 11 introduced in a blood vessel 10, for example an artery, having an open tip 110 located within the blood vessel 10 in the blood B flowing therein and having an open end 111 located outside the blood vessel 10 and through a fluid channel 19 leading from the inside of the cannula 11 to the sensor means 100, being brought thereto as baseline fluid BF from the hose 12 or as calibration fluid C or other calibration fluid from the hose 16.

The calibration of a sensor 1, 2, etc. and a blood value measurement with this sensor can be implemented as disclosed by EP 0 790 499 A2, i.e. a calibration of the sensor 1, 2 etc., ensues with the baseline fluid BF, with the calibration fluid C and potentially with another calibration fluid that differs in the value of the $pCO_2$ for the $CO_2$ sensor, in the pH value for the pH sensor and/or in the concentration of the ion-type for an ion-type sensor, differing, namely, from the calibration fluid C and serving for the calibration of a sensitivity of this sensor. An example is the other calibration fluid C' acquired from the calibration fluid C according to EP 0 790 499 A2 that differs from the calibration fluid C in terms of the value of $pCO_2$ and serves for calibrating the sensitivity of the $CO_2$ sensor 1 therein.

The potentiometric sensor 3 shown schematically in section in FIG. 2, which can be contained in the sensor means 100 of FIG. 1, is composed, for example of a housing 30 with a cavity, a measuring electrode 31 and a reference electrode 32.

The cavity is composed of a chamber 33 connected to the fluid channel 19 of FIG. 1 and of a spur channel 34 connected to the chamber 33 and leading away therefrom.

The chamber 33 is filled with inventive calibration fluid through the fluid channel 19 for calibrating the sensor 3 and is filled with blood B for measuring a blood value. This calibration fluid forms the base fluid BF, calibration fluid C or the other calibration fluid, for example the fluid C'.

The measuring electrode 31 is arranged such in the region of the chamber 33 that it is in contact with the respective fill BF, C, C' or B of the chamber 33.

The reference electrode 32 is arranged such at a distance from the chamber 33 and the measuring electrode 31 in the region of the spur channel that it is in contact with the fill of the spur channel 34. This fill is always composed of inventive calibration fluid, i.e. of base fluid BF, calibration fluid C or some other calibration fluid, for example the fluid C', since a measurement of a blood value is always preceded by a calibration with inventive calibration fluid wherein the entire cavity 33 and 34 is filled with this fluid, but only the chamber 33 is filled with blood B in the measurement of the blood values but inventive calibration fluid remains in the spur channel 34.

This remaining calibration fluid forms a bridge electrolyte that connects the reference electrode 32 to the blood B and, thus, to the measuring electrode 31. Due to the inventive properties of the fluid, a diffusion voltage of at most less than 1 mV that causes no measuring errors in the blood value measurement forms at the boundary surface 35 between the calibration fluid remaining in the spur channel 34 and the blood B in the chamber 33.

U.S. Pat. No. 5,385,659 discloses a sensor similar to the sensor 3 of FIG. 2. Each of the sensors 1, 2, etc. contained in the sensor means 100 according to FIG. 1 can be a sensor of the species of the sensor 3 of FIG. 2 insofar as they are potentiometric sensors.

I claim:

1. Calibration fluid for calibration of a sensor for measuring a blood value, comprising (i) a biocompatible electrolyte that at 37° C. exhibits a concentration of bicarbonate ions of about 24 mmol/l±5 mmol/l, a pH value that is in the range of 5 through 9 including a value 7.41, and has an ionic strength of about 155 mmol/l±10 mmol/l, and (ii) other ion types contained in normal, physiological blood, wherein said ion types are contained in the fluid in concentrations substantially equivalent to normal physiological concentrations of said ion types in blood such that a diffusion voltage of less than 1 mV occurs at a boundary surface between the fluid and normal, physiological blood; said fluid further comprising an organic physiological buffer.

2. Fluid according to one claim 1, which has an osmolarity that lies in the range 295 mosmol/l±20 mosmol/l.

3. Fluid according to claim 1, which has a pH value in the range between 6.6 and 8.0.

4. Fluid according to claim 1, wherein the organic buffer is defined by a specific Tris/TrisH$^+$ ratio.

5. Fluid according to claim 1 wherein the organic buffer is defined by a specific R-PO$_4^{2-}$/R-HPO$_4^-$ ratio wherein R is an organic radical.

6. Fluid according to claim 1, which has a sum of all partial pressures of the fluid that is lower than a pressure that bears on the fluid.

7. Fluid according to claim 6, wherein the partial pressure of N$_2$ at 37° C. in the fluid is lower than a value of this pressure in normal, physiological blood at this temperature.

8. Fluid according to claim 7, wherein the N$_2$ partial pressure of the fluid is essentially equal to zero.

9. A method for measuring a blood value comprising the steps of providing a calibration fluid composed of (i) a biocompatible electrolyte that at 37° C. exhibits a concentration of bicarbonate of about 24 mmol/l±5 mmol/l, a pH value in a range of 5 through 9, and an ionic strength that is about 155 mmol/l±10 mmol/l, and (ii) other ion types contained in normal, physiological blood, wherein said ion types are contained in the fluid in concentrations substantially equivalent to normal physiological concentrations of said ion types in blood such that a diffusion voltage of less than 1 mV occurs at a boundary surface between the fluid and normal, physiological blood, said fluid further containing an organic physiological buffer; providing a potentiometric sensor having a measuring electrode for measuring a blood value and a reference electrode; and using the fluid as a bridging electrolyte between the measuring electrode and the reference electrode.

10. A method of manufacturing a calibration fluid comprising (i) a biocompatible electrolyte that at 37° C. exhibits a concentration of bicarbonate ions of about 24 mmol/l±5 mmol/l, a pH value in a range of 5 through 9, and an ionic strength of about 155 mmol/l±10 mmol/l, and (ii) other ion types contained in normal, physiological blood, wherein said ion types are contained in the fluid in concentrations substantially equivalent to normal physiological concentrations of said ion types in blood such that a diffusion voltage of less than 1 mV occurs at a boundary surface between the fluid and normal, physiological blood, said fluid further containing an organic physiological buffer, said method comprising dissolving a specific quantity of an essentially salt-free, aqueous solvent NaHCO$_3$ together with at least one other biocompatible salt of a weight ratio relative to one another such that the calibration fluid subsequently exhibits a bicarbonate ion concentration at 37° C. in a normal physiological range of blood, a pH value in a range of 5 through 9 including a value 7.41 and an ionic strength in a range similar to normal physiological blood.

* * * * *